(12) United States Patent
Hattori et al.

(10) Patent No.: US 11,864,731 B2
(45) Date of Patent: Jan. 9, 2024

(54) CONNECTOR DEVICE FOR ENDOSCOPE

(71) Applicant: FUJIFILM Corporation, Tokyo (JP)

(72) Inventors: Shintaro Hattori, Kanagawa (JP); Nobuyuki Torisawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 322 days.

(21) Appl. No.: 17/407,123

(22) Filed: Aug. 19, 2021

(65) Prior Publication Data

US 2021/0382292 A1 Dec. 9, 2021

Related U.S. Application Data

(63) Continuation of application No. PCT/JP2020/011160, filed on Mar. 13, 2020.

(30) Foreign Application Priority Data

Mar. 19, 2019 (JP) ................. 2019-050667

(51) Int. Cl.
*A61B 1/00* (2006.01)
*G02B 23/24* (2006.01)
*A61B 1/313* (2006.01)

(52) U.S. Cl.
CPC ...... *A61B 1/00126* (2013.01); *G02B 23/2469* (2013.01); *A61B 1/313* (2013.01)

(58) Field of Classification Search
CPC . A61B 1/00126; A61B 1/313; A61B 1/00121; A61B 1/00137; G02B 23/2469;

(Continued)

(56) References Cited

U.S. PATENT DOCUMENTS

| 4,302,066 | A | 11/1981 | Newman et al. |
| 6,155,862 | A | 12/2000 | Chiu et al. |
| 10,993,605 | B2 * | 5/2021 | Levy .................. A61B 1/00165 |

FOREIGN PATENT DOCUMENTS

| CN | 106025714 | 10/2016 |
| JP | H0966024 | 3/1997 |
| JP | 2016064050 | 4/2016 |

OTHER PUBLICATIONS

"International Search Report (Form PCT/ISA/210) of PCT/JP2020/011160," dated May 19, 2020, with English translation thereof, pp. 1-5.

(Continued)

*Primary Examiner* — John Bedtelyon
(74) *Attorney, Agent, or Firm* — JCIPRNET

(57) ABSTRACT

A connector device for an endoscope that can prevent infiltration of water into an exterior member is provided. A linear portion (46A) of an elliptical ring portion (46) of a connector exterior case (28) includes through-holes (50 and 52). An inner peripheral surface of the linear portion (46A) includes a semicircular groove (54) that connects the through-hole (50) and the through-hole (52) to each other. An outer peripheral surface of a linear portion (30A) of an elliptical ring portion (30) of a plug (26) includes a semicircular groove (56), and the groove (56) is disposed to face the groove (54) so that an insertion passage (58) is formed. A pin (60) is fitted into the through-hole (52) from the through-hole (50) via the insertion passage (58), and the pin (60) is fitted to the through-hole (50), the insertion passage (58), and the through-hole (52).

16 Claims, 11 Drawing Sheets

(58) Field of Classification Search
CPC . G02B 23/2492; G02B 6/3817; G02B 6/3897
See application file for complete search history.

(56) References Cited

OTHER PUBLICATIONS

"Written Opinion of the International Searching Authority (Form PCT/ISA/237)" of PCT/JP2020/011160, dated May 19, 2020, with English translation thereof, pp. 1-6.
"Search Report of Europe Counterpart Application", dated Apr. 7, 2022, p. 1-p. 10.

* cited by examiner

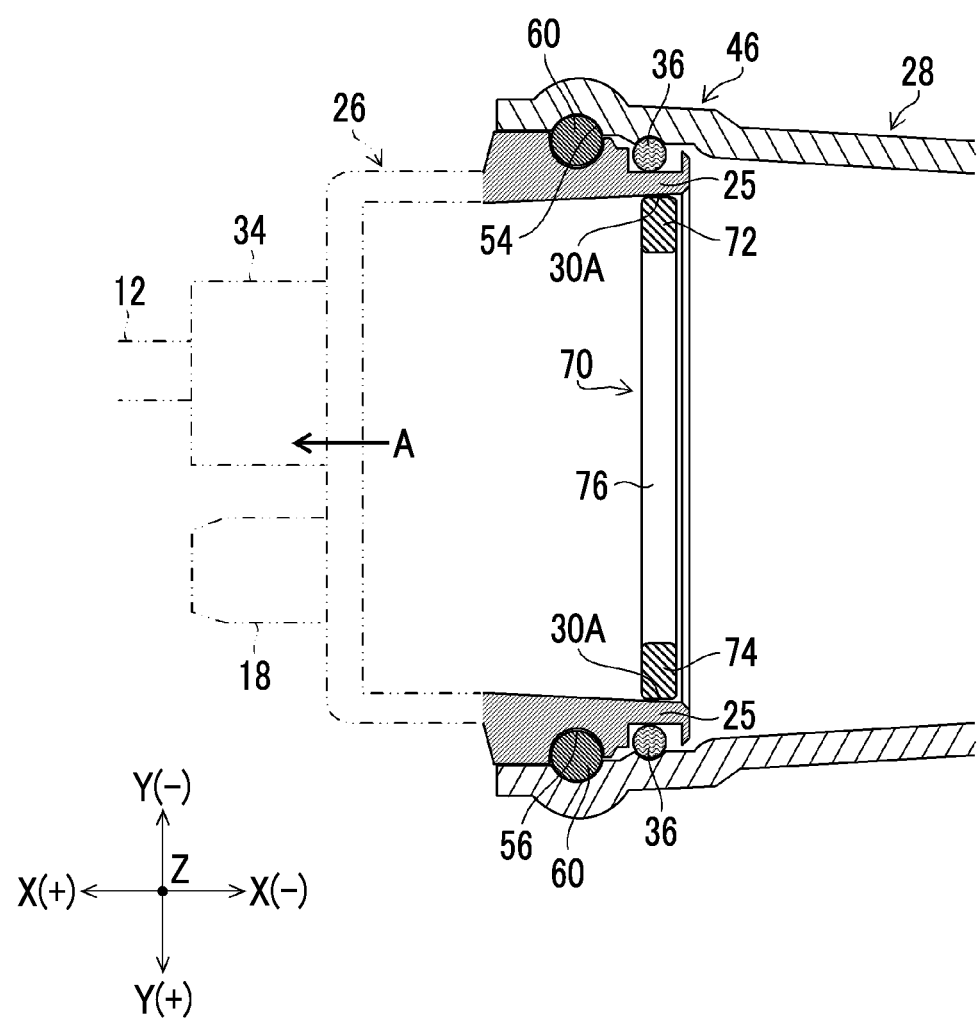

CONNECTOR DEVICE FOR ENDOSCOPE

CROSS-REFERENCE TO RELATED APPLICATIONS

The present application is a Continuation of PCT International Application No. PCT/JP2020/011160 filed on Mar. 13, 2020 claiming priority under 35 U.S.C § 119(a) to Japanese Patent Application No. 2019-050667 filed on Mar. 19, 2019. Each of the above applications is hereby expressly incorporated by reference, in its entirety, into the present application.

BACKGROUND OF THE INVENTION

1. Field of the Invention

The present invention relates to a connector device for an endoscope, and particularly relates to a connector device for an endoscope provided at a tip part of a universal cable of an endoscope.

2. Description of the Related Art

Among endoscopes, an electronic endoscope transmits irradiation light from a light source device with a light guide so that an observation part is irradiated with the irradiation light, and images the observation part with a solid-state imaging element. Then, a processor performs image processing on an electric signal output from the solid-state imaging element, and an observed image is displayed on a TV monitor. In such an electronic endoscope, a universal cable is extended from a hand operating part of the electronic endoscope, and a connector device is provided at a tip part of the universal cable. The connector device is provided with a light guide rod that is connected to the light source device and a connector that is connected to a processor device (see JP1997-66024A (JP-H9-66024A)).

The connector device for an endoscope disclosed in JP1997-66024A (JP-H9-66024A) comprises a synthetic resin exterior member having a base and a case body. A metal body frame is fixed to the base by a screw and a nut. In addition, the base has an attaching surface, an annular attaching groove is formed along an outer periphery of the attaching surface, and an O-ring is disposed in the attaching groove. On the other hand, the case body has an opening portion, and an annular fitting protrusion fitted to the attaching groove is formed around the opening portion. Accordingly, in the connector device of JP1997-66024A (JP-H9-66024A), the base and the case body are connected to each other by fitting the fitting protrusion of the case body to the attaching groove of the base via the O-ring.

SUMMARY OF THE INVENTION

It is necessary for, for example, a rigid scope used in laparoscopic surgery to be sterilized each time the rigid scope is used. In this case, sterilization is performed using an autoclave in some cases, but the rigid scope and the connector device at the time of sterilization are exposed to high-temperature and high-pressure (for example, 121° C. and 2 atm) saturated steam for approximately 20 minutes.

However, in the connector device for an endoscope of JP1997-66024A (JP-H9-66024A), in a case where the connector device is exposed to a vacuum state at a high temperature during sterilization or after sterilization, the internal pressure of the exterior member becomes higher than the external pressure of the exterior member. Thus, a force caused by a differential pressure concentrates on a connecting part between the base and the case body, and the connecting part is deformed or damaged in some cases due to the force. In such a case, there is a problem that water infiltrates into the exterior member.

The present invention is devised in view of such circumstances, and an object thereof is to provide a connector device for an endoscope that can prevent infiltration of water into an exterior member.

According to an aspect of the present invention, in order to achieve the object of the present invention, there is provided a connector device for an endoscope comprising an exterior member that includes a plug which has an annular first connecting part forming a first opening in an end part thereof and a connector exterior case which has an annular second connecting part forming a second opening in an end part thereof. The first connecting part has at least a pair of first linear portions facing each other. The second connecting part has at least a pair of second linear portions facing each other. An outer peripheral surface of the first linear portion has a first groove along the first linear portion. An inner peripheral surface of the second linear portion has a second groove along the second linear portion. The second linear portion has a first through-hole that penetrates an outer peripheral surface and an inner peripheral surface of the second connecting part and is connected to one end side of the second groove and a second through-hole that penetrates the outer peripheral surface and the inner peripheral surface of the second connecting part and is connected to the other end side of the second groove. The first groove and the second groove face each other so that an insertion passage along the first linear portion and the second linear portion is formed in a state where the outer peripheral surface of the first linear portion is fitted into the inner peripheral surface of the second linear portion so that the plug and the connector exterior case are connected to each other. The connector device for an endoscope further comprises a shaft member that is fitted into the second through-hole from the first through-hole via the insertion passage and is fitted to the first through-hole, the insertion passage, and the second through-hole.

In the aspect of the present invention, it is preferable that the pair of first linear portions are disposed to be parallel to each other, and the pair of second linear portions are disposed to be parallel to each other.

In the aspect of the present invention, it is preferable that the connector device for an endoscope further comprises a fastening member that fastens the shaft member and the plug to each other.

In the aspect of the present invention, it is preferable that the connector device for an endoscope further comprises a first sealing member disposed between an outer peripheral surface of the first connecting part and the inner peripheral surface of the second connecting part.

In the aspect of the present invention, it is preferable that the first sealing member is an O-ring fitted to the outer peripheral surface of the first connecting part.

In the aspect of the present invention, it is preferable that the connector device for an endoscope further comprises a reinforcing member of which one end abuts against an inner peripheral surface of one first linear portion of the pair of first linear portions and the other end abuts against an inner peripheral surface of the other first linear portion.

In the aspect of the present invention, it is preferable that the shaft member is a cylindrical member.

In the aspect of the present invention, it is preferable that a shield case is accommodated inside the exterior member, and the reinforcing member is fixed to the shield case.

In the aspect of the present invention, it is preferable that the connector device for an endoscope further comprises a shaft-shaped member of which one end is fixed to the shield case, a first lead-out hole that is formed in the plug and leads the shaft-shaped member to an outside, and a second sealing member that is disposed between an outer wall surface of the shaft-shaped member and an inner wall surface of the first lead-out hole.

In the aspect of the present invention, it is preferable that the shield case is disposed to be spaced apart from an inner surface of the exterior member as the shield case is held by the plug only via the second sealing member.

In the aspect of the present invention, it is preferable that the second sealing member is an O-ring fitted to the outer wall surface of the shaft-shaped member.

In the aspect of the present invention, it is preferable that the connector exterior case has an opening portion to which a universal cable extending from an endoscope is connected, and a third sealing member is disposed between an outer wall surface of the universal cable and an inner wall surface of the opening portion.

In the aspect of the present invention, it is preferable that the third sealing member is an O-ring fitted to the outer wall surface of the universal cable.

In the aspect of the present invention, it is preferable that the opening portion of the connector exterior case is formed in a size that allows the endoscope, the universal cable, and a switch disposed member provided at the universal cable to be inserted therein.

In the aspect of the present invention, it is preferable that the connector device for an endoscope further comprises a light guide rod of which one end is fixed to the plug, a second lead-out hole that is formed in the plug and leads the light guide rod to an outside, and a fourth sealing member that is disposed between an outer wall surface of the light guide rod and an inner wall surface of the second lead-out hole.

In the aspect of the present invention, it is preferable that the fourth sealing member is an O-ring fitted to the outer wall surface of the light guide rod.

With the present invention, the infiltration of water into the exterior member can be prevented.

BRIEF DESCRIPTION OF THE DRAWINGS

FIG. 13 is a cross sectional view of main parts, taken along line XIII-XIII of FIG. 12.

DESCRIPTION OF THE PREFERRED EMBODIMENTS

Hereinafter, a connector device for an endoscope according to an embodiment of the present invention will be described with reference to the accompanying drawings.

Figure 1:
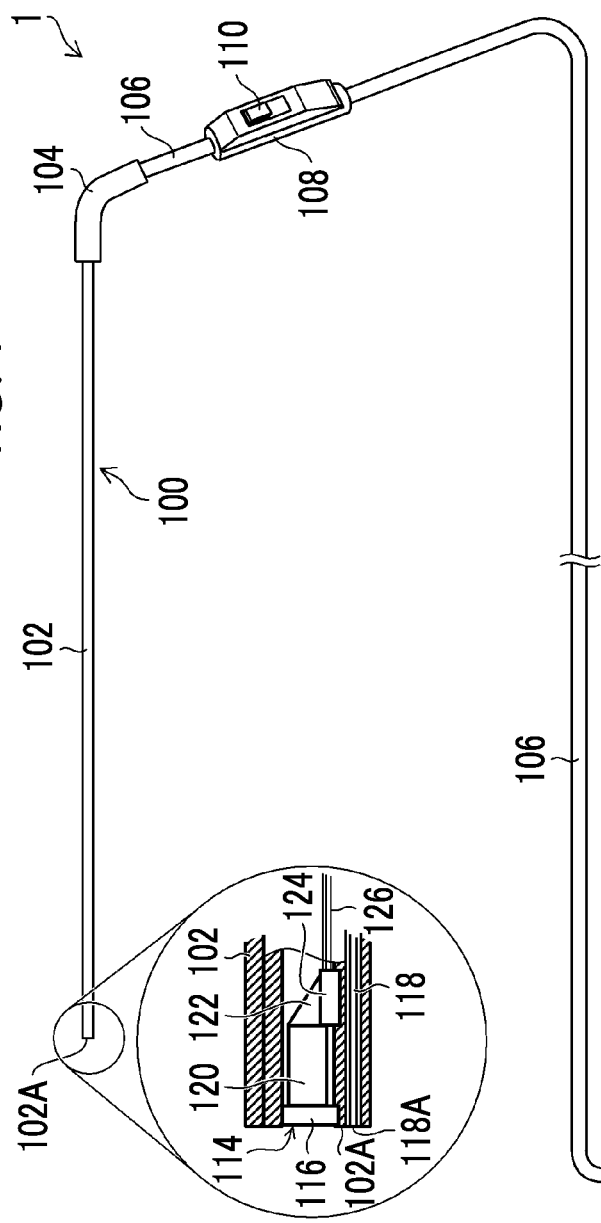
FIG. 1 is a schematic configuration view of an endoscope system.
Figure 1:
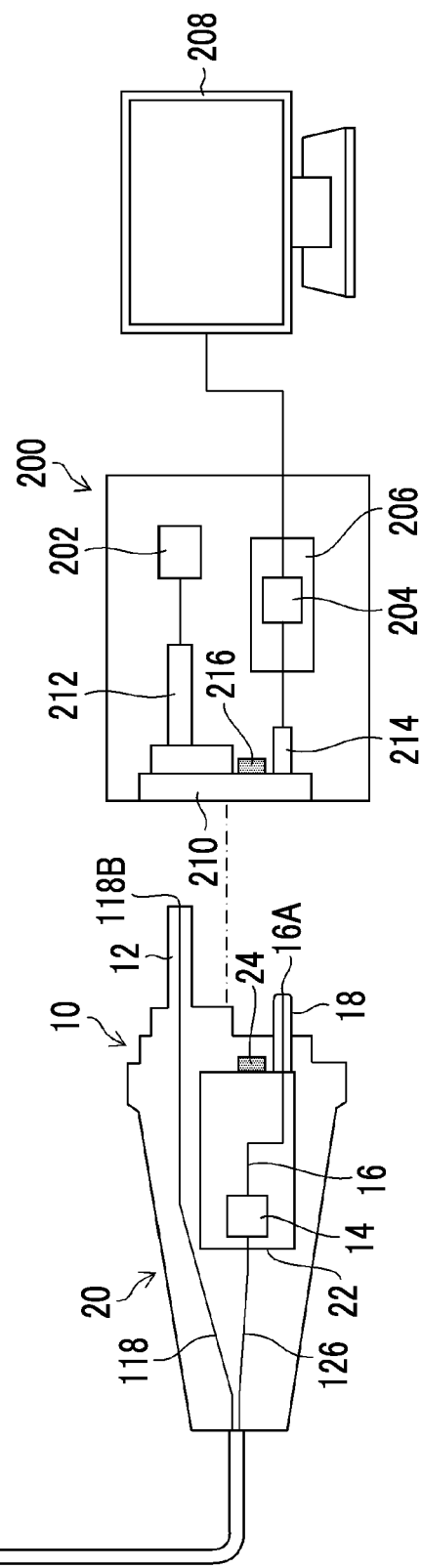

FIG. 1 is a schematic configuration view of an endoscope system 1. The endoscope system 1 comprises an endoscope 100 and a processor device for an endoscope 200.

The endoscope 100 is a rigid endoscope, such as a laparoscope, and comprises an elongated rigid insertion part 102 that is inserted into a body cavity, an L-shaped grip portion 104 continuously connected to a proximal end part of the insertion part 102, a flexible universal cable 106 of which a proximal end part is connected to the insertion part 102 via the grip portion 104, and a switch disposed member 108 provided in a middle portion of the universal cable 106.

A connector device 10 according to the embodiment is provided at a tip part of the universal cable 106, and the endoscope 100 is attachably and detachably connected to a processor side connector 210 of the processor device for an endoscope 200 via the connector device 10. FIG. 1 illustrates the connector device 10 in an exaggerated manner as compared with the endoscope 100.

The processor device for an endoscope 200 comprises an image processing unit 206, which includes a light source unit 202, and an image signal reception unit 204. In addition, a monitor 208 that displays an image which is image-processed by the image processing unit 206 is connected to the processor device for an endoscope 200.

The endoscope system 1 of the present example has a configuration that transmits power, optical signals, and the like in a contactless manner between the endoscope 100 and the processor device for an endoscope 200 via a connector part composed of the connector device 10 and the processor side connector 210. In addition, as an operation switch 110 disposed on the switch disposed member 108 described above, for example, an image changeover switch that switches an image to be displayed on the monitor 208 between a normal captured image and a special light image (for example, a white light (WL) image, a blue laser imaging (BLI) image, a linked color imaging (LCI) image, or a hypoxia imaging image) can be applied. In addition, without being limited to the image changeover switch, an image immobilizing switch, an imaging switch, a zoom switch comprising a telephoto and wide-angle button, a insertion part tip part washing switch, a light amount adjusting switch, a sensitivity adjusting switch, or the like can also be applied.

Figure 2:
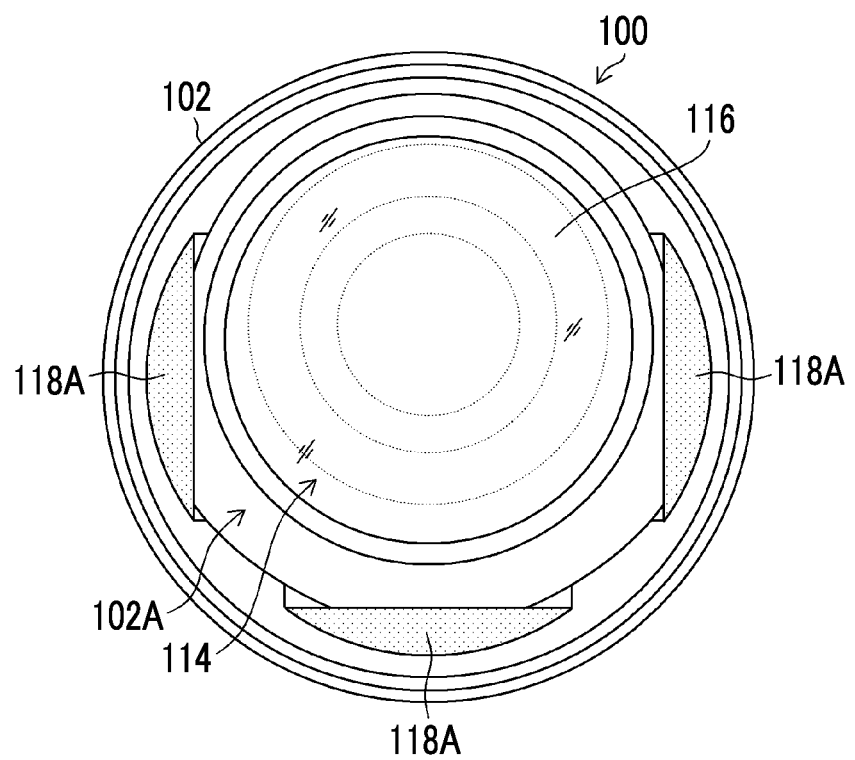
FIG. 2 is a front view of a tip part of an insertion part.

FIG. 2 is a front view of a tip part of the insertion part 102. In addition, FIG. 1 illustrates an enlarged cross section of main parts at the tip part of the insertion part 102.

As illustrated in FIGS. 1 and 2, an observation part 114 is provided on a distal end surface 102A of the insertion part 102. The observation part 114 comprises an observation window 116, three light emission ends 118A that are tip parts of a light guide 118, which is disposed around the observation window 116, an image pick-up lens group 120 and a prism 122 that are disposed behind the observation window 116, and a solid-state imaging element 124. As the solid-state imaging element 124, a charge coupled device (CCD) image sensor or a complementary metal oxide semiconductor (CMOS) image sensor can be applied.

A proximal end part of the light guide 118 is inserted into the insertion part 102, the grip portion 104, and the universal cable 106, and is disposed to be inserted in a cylindrical light guide rod 12 of the connector device 10. By connecting the light guide rod 12 to a connection hole 212 of the processor side connector 210, a light incident end 118B of the light guide 118 is connected to the light source unit 202 of the processor device for an endoscope 200. Accordingly, illumination light from the light source unit 202 is transmitted via the light guide 118, and is radiated to the front of the insertion part 102 from the three light emission ends 118A of the light guide 118.

On the other hand, subject light picked up from the observation window 116 is formed as an image on an imaging surface of the solid-state imaging element 124 via the image pick-up lens group 120 and the prism 122, and is converted to an image pick-up signal by the solid-state imaging element 124. A tip part of a signal line 126 is connected to the solid-state imaging element 124 via a base substrate (not illustrated). A proximal end part of the signal line 126 is inserted into the insertion part 102, the grip portion 104, and the universal cable 106, and is connected to an image signal transmission unit 14 accommodated in an exterior member 20 of the connector device 10. The image pick-up signal is converted to an optical signal by the image signal transmission unit 14, and the optical signal is transmitted to a fiber cable 16 accommodated in the exterior member 20.

A light emission end 16A of the fiber cable 16 is disposed to be inserted in a cylindrical pin 18 of the connector device 10. By connecting the pin 18 to a connection hole 214 of the processor side connector 210, the optical signal is optically transmitted to the image signal reception unit 204 of the processor device for an endoscope 200 in a contactless manner. The optical signal optically transmitted to the image signal reception unit 204 is image-processed by the image processing unit 206 and is displayed on the monitor 208 as a subject image.

The pin 18 is an example of a shaft-shaped member, which is a component of the present invention. A proximal end part of the pin 18 is fixed to a metal shield case 22 accommodated inside the exterior member 20, and the shield case 22 is positioned at the processor side connector 210 by connecting the pin 18 to the connection hole 214. In addition, an electronic component such as a substrate configuring the image signal transmission unit 14 is mounted inside the shield case 22.

The connector device 10 is provided with a power reception unit 24 that receives power in a contactless manner, and the processor side connector 210 is provided with a power feed unit 216 that feeds power in a contactless manner. In the endoscope system 1 of the present example, a contactless power supply unit is composed of the power feed unit 216 and the power reception unit 24, and power necessary for driving an electronic component on an endoscope 100 side is supplied by the power supply unit from the processor device for an endoscope 200 to the connector device 10.

In a case where the connector device 10 is connected to the processor side connector 210 via the light guide rod 12 and the pin 18, the power feed unit 216 and the power reception unit 24 are disposed near to face each other at a distance allowing electromagnetic coupling, and are in a state where power feeding from the power feed unit 216 to the power reception unit 24 is possible in a contactless manner. In addition, the power feed unit 216 is connected to an external commercial power source, and in a case where power is supplied from the commercial power source to the power feed unit 216, power is fed in a contactless manner from the power feed unit 216 to the power reception unit 24.

A primary coil (also referred to as a power feeding coil) connected to the commercial power source can be given as an example of the power feed unit 216, and a secondary coil (also referred to as a power reception coil) electromagnetically coupled to the primary coil can be given as an example of the power reception unit 24. Since an endoscope that feeds power using such a primary coil and such a secondary coil is known in JP2016-67534A, detailed description thereof will be omitted herein.

Figure 3:
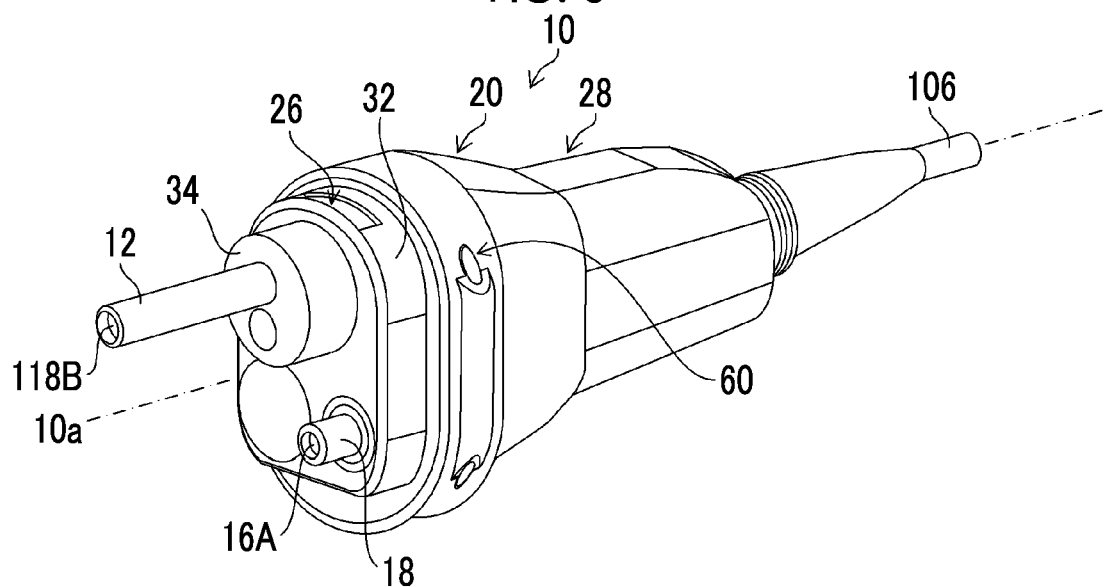
FIG. 3 is an external perspective view of a connector device.

Next, a structure of the connector device 10 will be described. FIG. 3 is an overall perspective view illustrating the appearance of the connector device 10.

As illustrated in FIG. 3, the exterior member 20 of the connector device 10 has a longitudinal axis 10a parallel to an axial direction of the cylindrical light guide rod 12 and the pin 18. In the following description, a position and a direction of a space where the connector device 10 is disposed will be described using the following terms. An X(+) direction and an X(−) direction along the longitudinal axis 10a are the "front" and the "rear" respectively, a Y(+) direction and a Y(−) direction orthogonal to the X-direction are the "left" and the "right" respectively, and a Z(+) direction and a Z(−) direction orthogonal to the XY-directions are the "up" and the "down" respectively.

The connector device 10 has the highly heat-resistant and chemical-resistant resin exterior member 20, the metal light guide rod 12, the metal pin 18, and the metal shield case 22 (see FIG. 1).

Figure 4:
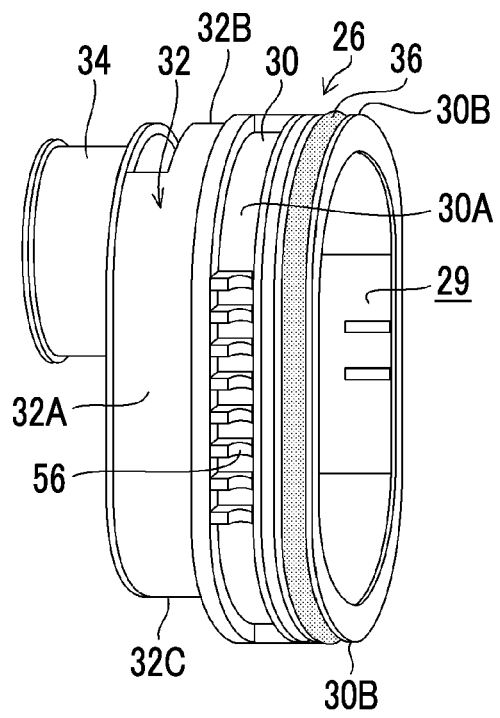
FIG. 4 is a perspective view of a plug configuring an exterior member.
Figure 5:
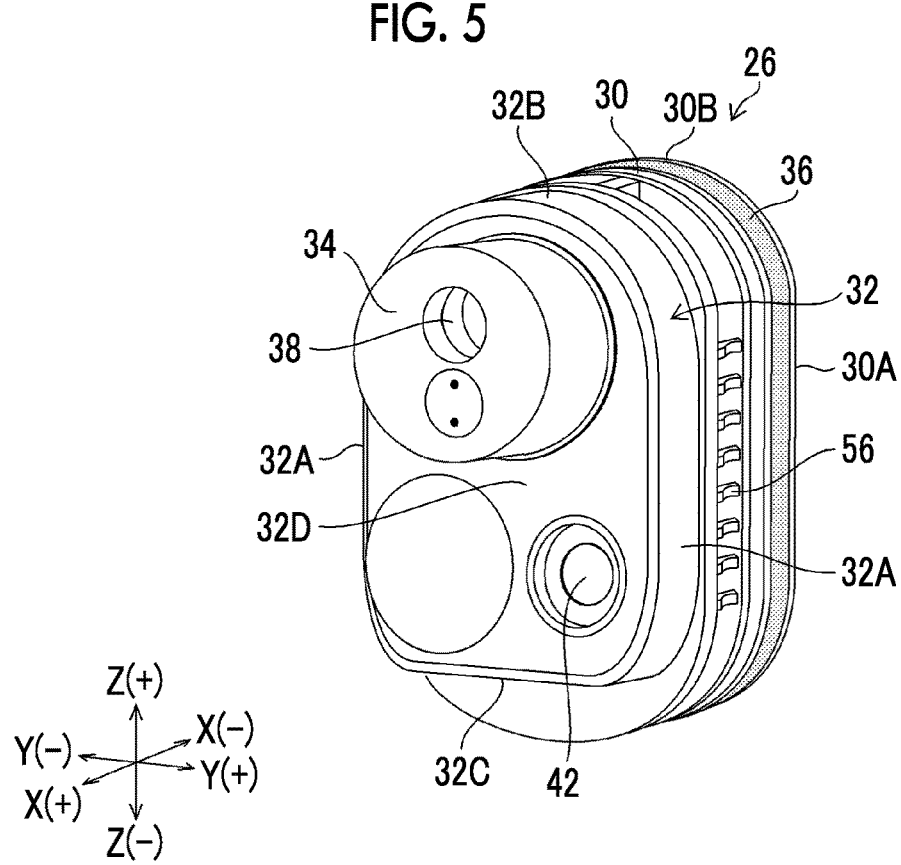
FIG. 5 is a perspective view of the plug viewed from the front toward the rear.
Figure 6:
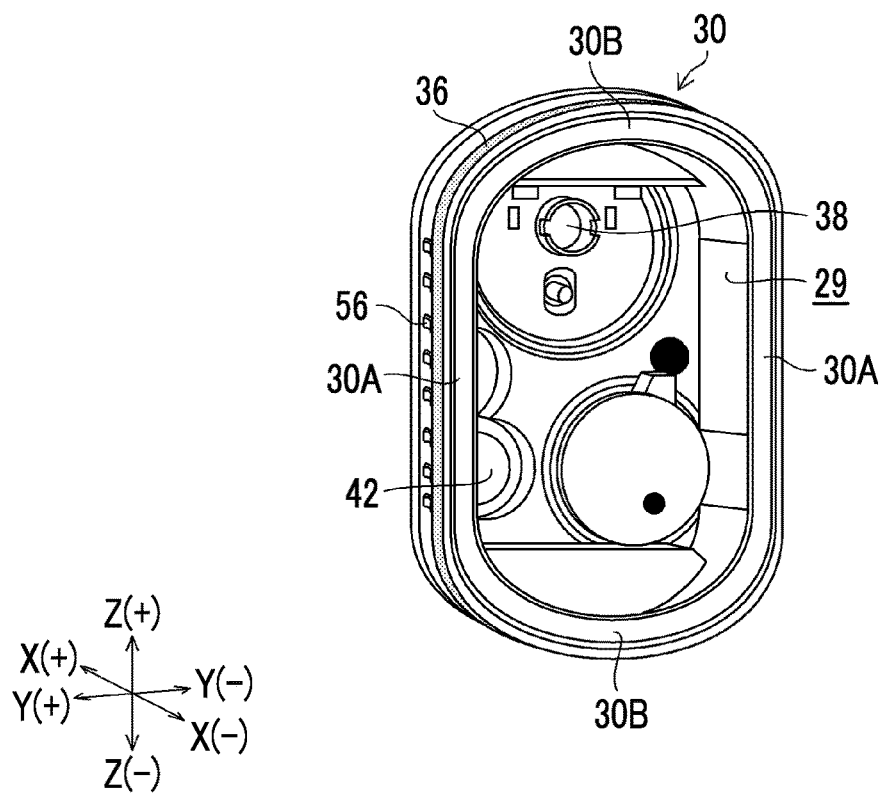
FIG. 6 is a perspective view of the plug viewed from the rear toward the front.

FIG. 4 is a perspective view of a plug 26 configuring the exterior member 20. FIG. 5 is a perspective view of the plug 26 viewed from the front toward the rear. FIG. 6 is a perspective view of the plug 26 viewed from the rear toward the front.

Figure 7:
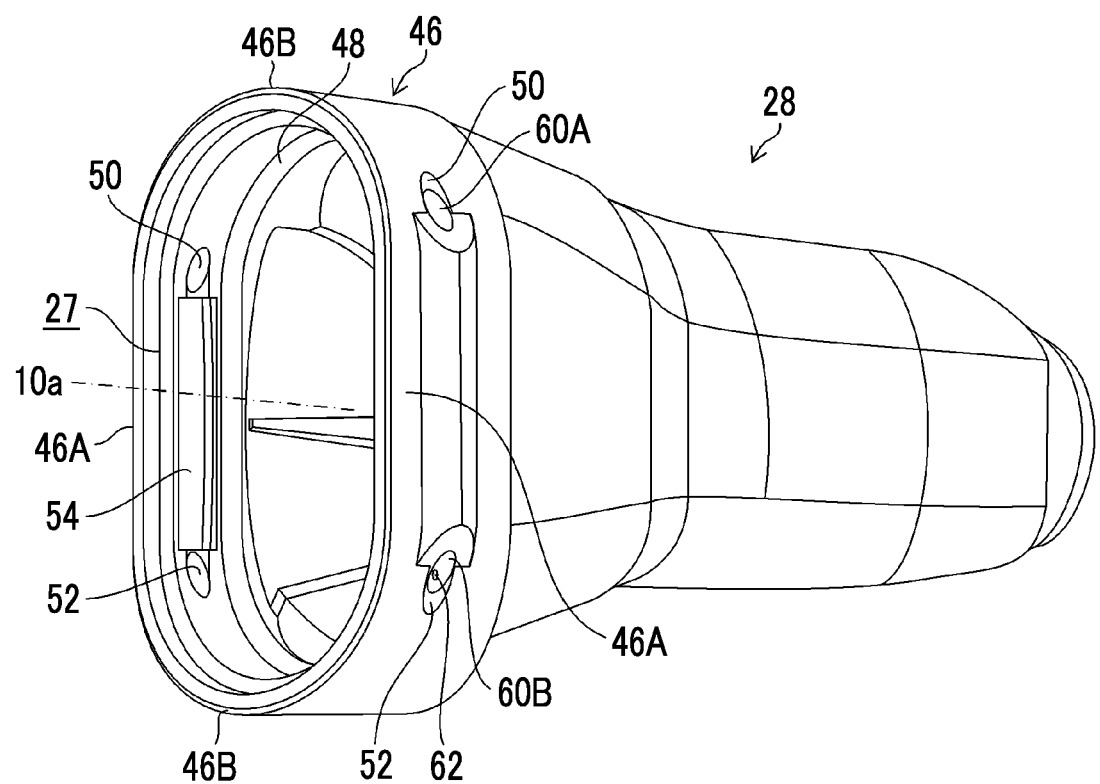
FIG. 7 is a perspective view of a connector exterior case configuring the exterior member viewed from the front toward the rear.
Figure 7:
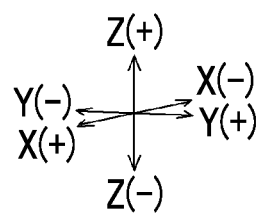
Figure 8:
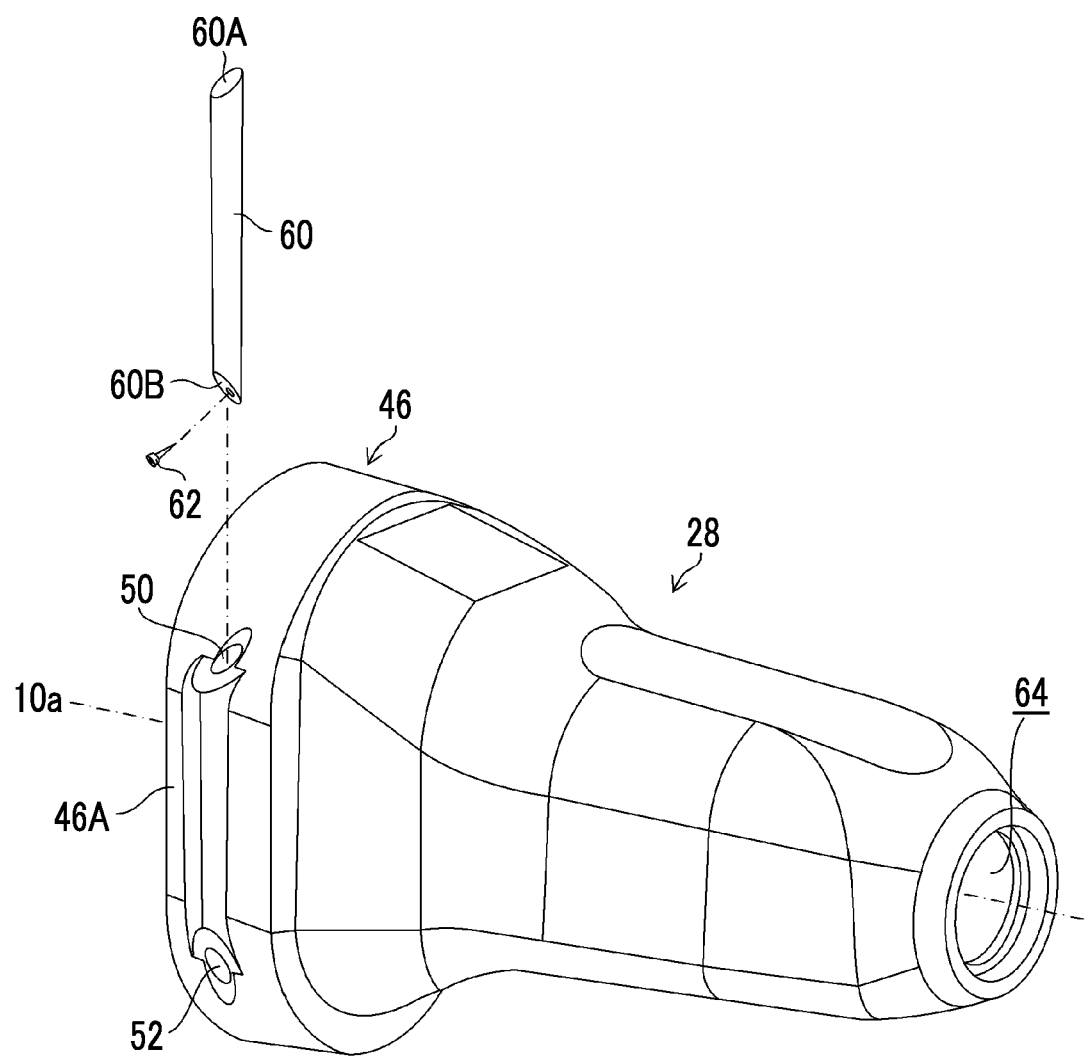
FIG. 8 is a perspective view of the connector exterior case viewed from the rear toward the front.
Figure 8:
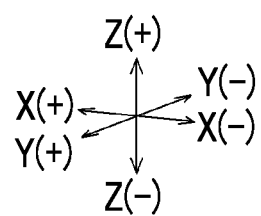

In addition, FIG. 7 is a perspective view of a connector exterior case 28 configuring the exterior member 20 viewed from the front toward the rear. FIG. 8 is a perspective view of the connector exterior case 28 viewed from the rear toward the front.

Referring back to FIG. 3, the exterior member 20 is formed in a hollow shape by connecting the plug 26 illustrated in FIGS. 4 to 6 to the connector exterior case 28 illustrated in FIGS. 7 and 8.

As illustrated in FIGS. 4 to 6, the plug 26 comprises an elliptical ring portion 30 that has an opening 29 in a rear end, a mount portion 32 that protrudes from the elliptical ring portion 30 toward the front, and a cylindrical portion 34 that protrudes from the mount portion 32 toward the front. The opening 29 is an example of a first opening, which is a component of the present invention, and the elliptical ring portion 30 is an example of an annular first connecting part, which is a component of the present invention.

As illustrated in FIG. 6, the elliptical ring portion 30 is configured to have a shape in plan view that is a race track shape (oval shape), in which a pair of parallel linear portions 30A and 30A, which face each other in a right-and-left direction, and a pair of curved portions 30B and 30B, which face each other in an up-and-down direction, are connected to each other. The linear portions 30A and 30A each are an example of a first linear portion, which is a component of the present invention.

An O-ring 36 is fitted to an outer peripheral surface of the elliptical ring portion 30. The O-ring 36 is an example of a first sealing member that is disposed between the outer peripheral surface of the elliptical ring portion 30 and an inner peripheral surface of an elliptical ring portion 46 (see FIG. 7) of the connector exterior case 28 and is a component of the present invention. In addition, the O-ring 36 is one of a plurality of sealing members that seal the inside of the exterior member 20.

As illustrated in FIG. 5, the mount portion 32 is configured to have a shape in plan view that is a semi-elliptical shape, in which a pair of parallel linear portions 32A and 32A, which face each other in the right-and-left direction, and the curved portion 32B and a linear portion 32C, which face each other in the up-and-down direction, are connected to each other.

The cylindrical portion 34 is provided on an upper part of a side wall part 32D of the mount portion 32 and comprises, in a center part thereof, a lead-out hole 38 that leads a tip part of the light guide rod 12 (see FIG. 3) to the outside. The lead-out hole 38 is an example of a second lead-out hole, which is a component of the present invention. In addition, in a case where the connector device 10 is connected to the processor device for an endoscope 200, a side wall part 32D is disposed to face the power feed unit 216 of the processor device for an endoscope 200.

Figure 9:
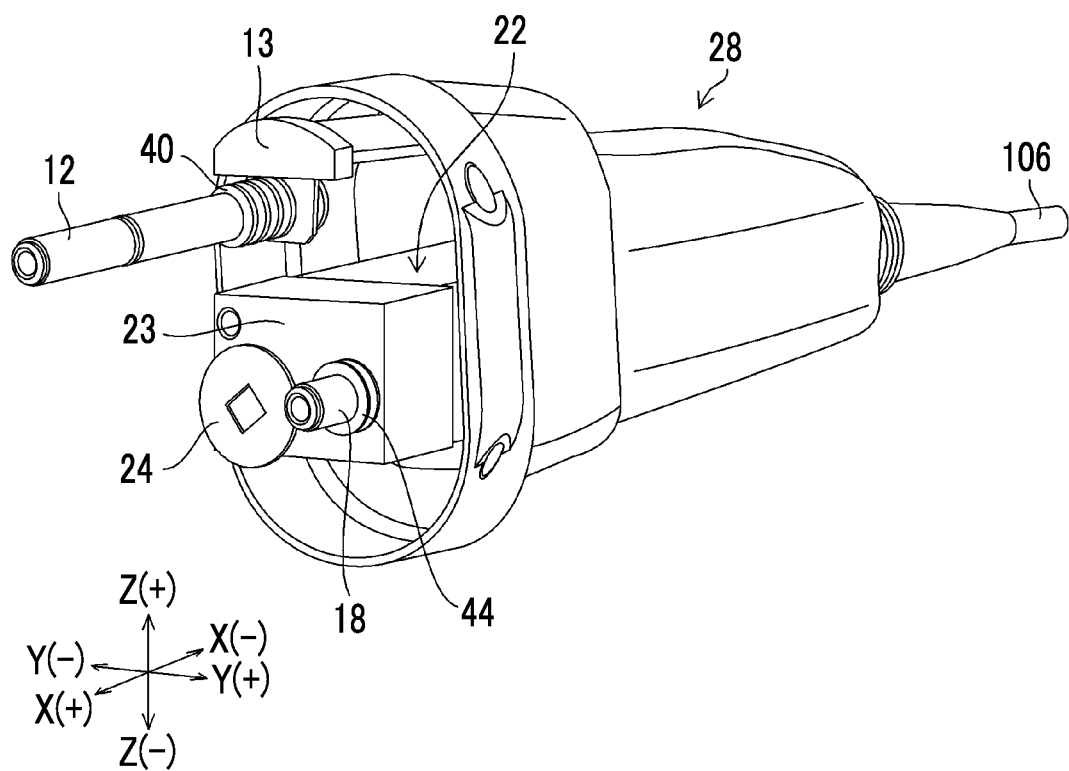
FIG. 9 is a perspective view of the connector exterior case including a light guide rod viewed from the front toward the rear.

FIG. 9 is a perspective view of the connector exterior case 28 viewed from the front toward the rear, and illustrates the light guide rod 12 and the shield case 22. As illustrated in FIG. 9, the light guide rod 12 has a proximal end part disposed inside the exterior member 20, and is fixed to a substantially semicircular bracket 13. As the bracket 13 is fixed to an inner peripheral surface of the plug 26 illustrated in FIGS. 4 to 6, the light guide rod 12 is supported by the plug 26.

In addition, as illustrated in FIG. 9, an elastic O-ring 40 is fitted to an outer peripheral surface of the light guide rod 12, and the light guide rod 12 is fitted into the lead-out hole 38 (see FIG. 5) via the O-ring 40. The O-ring 40 is an example of a fourth sealing member that is disposed between an outer peripheral surface configuring an outer wall surface of the light guide rod 12 and an inner peripheral surface configuring an inner wall surface of the lead-out hole 38 and is a component of the present invention. The O-ring 40 is also one of the plurality of sealing members that seal the inside of the exterior member 20, like the O-ring 36.

Referring back to FIG. 5, the side wall part 32D of the mount portion 32 comprises a lead-out hole 42 that leads the pin 18 (see FIG. 3) to the outside. The lead-out hole 42 is an example of a first lead-out hole, which is a component of the present invention.

As illustrated in FIG. 9, the proximal end part of the pin 18 is fixed to a case wall part 23, which is a front surface of the shield case 22, and a tip part of the pin 18 is disposed to face the front. In addition, an elastic O-ring 44 is fitted to an outer peripheral surface of the pin 18, and the pin 18 is fitted into the lead-out hole 42 (see FIG. 5) via the O-ring 44. The O-ring 44 is an example of a second sealing member that is disposed between an outer peripheral surface configuring an outer wall surface of the pin 18 and an inner peripheral surface configuring an inner wall surface of the lead-out hole 42 and is a component of the present invention. The O-ring 44 is also one of the plurality of sealing members that seal the inside of the exterior member 20, like the O-rings 36 and 40.

In addition, as the pin 18 is fitted into the lead-out hole 42 via the O-ring 44, the shield case 22 (see FIG. 1) to which the pin 18 is fixed is held by the plug 26 only via the O-ring 44, and is disposed to be spaced apart from inner surfaces of the plug 26 and the connector exterior case 28.

Figure 10:
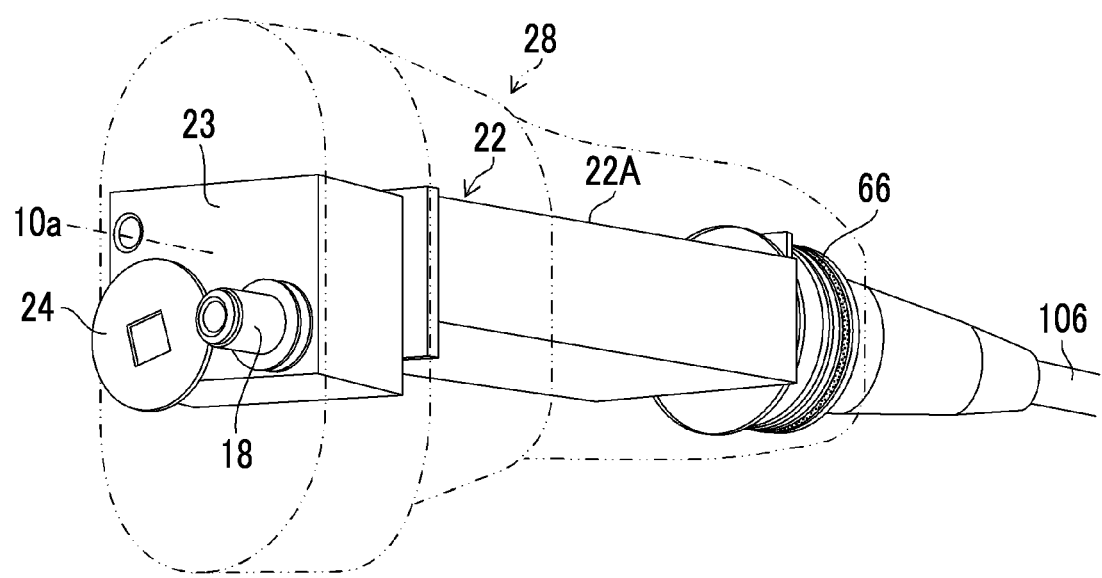
FIG. 10 is a perspective view illustrating a configuration of a shield case.
Figure 10:
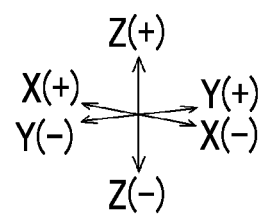

FIG. 10 is a perspective view illustrating a configuration of the shield case 22. As illustrated in FIG. 10, the shield case 22 is formed in a rectangular parallelepiped shape, and a long side 22A of the shield case 22 is accommodated in the connector exterior case 28 in a posture along the longitudinal axis 10a. Accordingly, a sufficient space is secured between the inner surface of the connector exterior case 28 and an outer surface of the shield case 22.

As illustrated in FIGS. 7 and 8, the connector exterior case 28 is formed in a substantially cylindrical shape with a bulging front end. The connector exterior case 28 comprises the elliptical ring portion 46 that has an opening 27 in the front end. The elliptical ring portion 46 is configured to have a shape in plan view that is a race track shape (oval shape), in which a pair of parallel linear portions 46A and 46A, which face each other in the right-and-left direction, and a pair of curved portions 46B and 46B, which face each other in the up-and-down direction, are connected to each other. Herein, the opening 27 is an example of a second opening, which is a component of the present invention, and the elliptical ring portion 46 is an example of an annular second connecting part, which is a component of the present invention. In addition, the linear portion 46A and 46A each are an example of a second linear portion, which is a component of the present invention. The pair of linear portions 46A and 46A are not limited to being parallel to each other, and may be not parallel to each other.

The connector exterior case 28 and the plug 26 (see FIG. 6) are connected to each other by fitting the elliptical ring portion 30 of the plug 26 into the elliptical ring portion 46 of the connector exterior case 28. In this connected state, the linear portions 30A and 30A of the elliptical ring portion 30 and the linear portions 46A and 46A of the elliptical ring portion 46 are disposed to face each other, and the curved portions 30B and 30B of the elliptical ring portion 30 and the curved portions 46B and 46B of the elliptical ring portion 46 are disposed to face each other. Then, as illustrated in FIG. 7, an inner peripheral surface of the elliptical ring portion 46 comprises an annular groove 48 along the inner peripheral surface, and the O-ring 36 (see FIG. 5) on a plug 26 side is fitted to the groove 48. That is, the connector exterior case 28 and the plug 26 are connected to each other by fitting the elliptical ring portion 30 of the plug 26 into the elliptical ring portion 46 of the connector exterior case 28 and fitting the O-ring 36 to the groove 48 (see FIG. 3).

On the other hand, as illustrated in FIG. 8, the linear portions 46A and 46A of the elliptical ring portion 46 comprises a pair of through-holes 50 and 52 (only the through-holes 50 and 52 in a left surface of the elliptical ring portion 46 are illustrated) penetrating an outer peripheral surface and the inner peripheral surface of the elliptical ring portion 46, which are coaxial in the up-and-down direction. In addition, as illustrated in FIG. 7, each of inner peripheral surfaces of the linear portions 46A and 46A comprises a semicircular groove 54, which connects the through-hole 50 and the through-hole 52 to each other, along the up-and-down direction. Further, as illustrated in FIGS. 4 and 5, outer peripheral surfaces of the linear portions 30A and 30A of the elliptical ring portion 30 comprise semicircular grooves 56 and 56 (only the grooves 56 in a left surface of the elliptical ring portion 30 are illustrated) along the up-and-down direction, and the grooves 56 are disposed to face the grooves 54 in a state where the connector exterior case 28 and the plug 26 are connected to each other. Accordingly, as in a cross sectional view of main parts illustrated in FIG. 11, a substantially cylindrical insertion passage 58 is formed along the up-and-down direction by a wall surface of the groove 54 and a wall surface of the groove 56. Herein, the through-holes 50 and 52 are an example of a first through-hole and an example of a second through-hole respectively, which are components of the present invention, and the groove 54 is an example of a second groove, which is a component of the present invention. In addition, the groove 56 is an example of a first groove, which is a component of the present invention.

Figure 11:
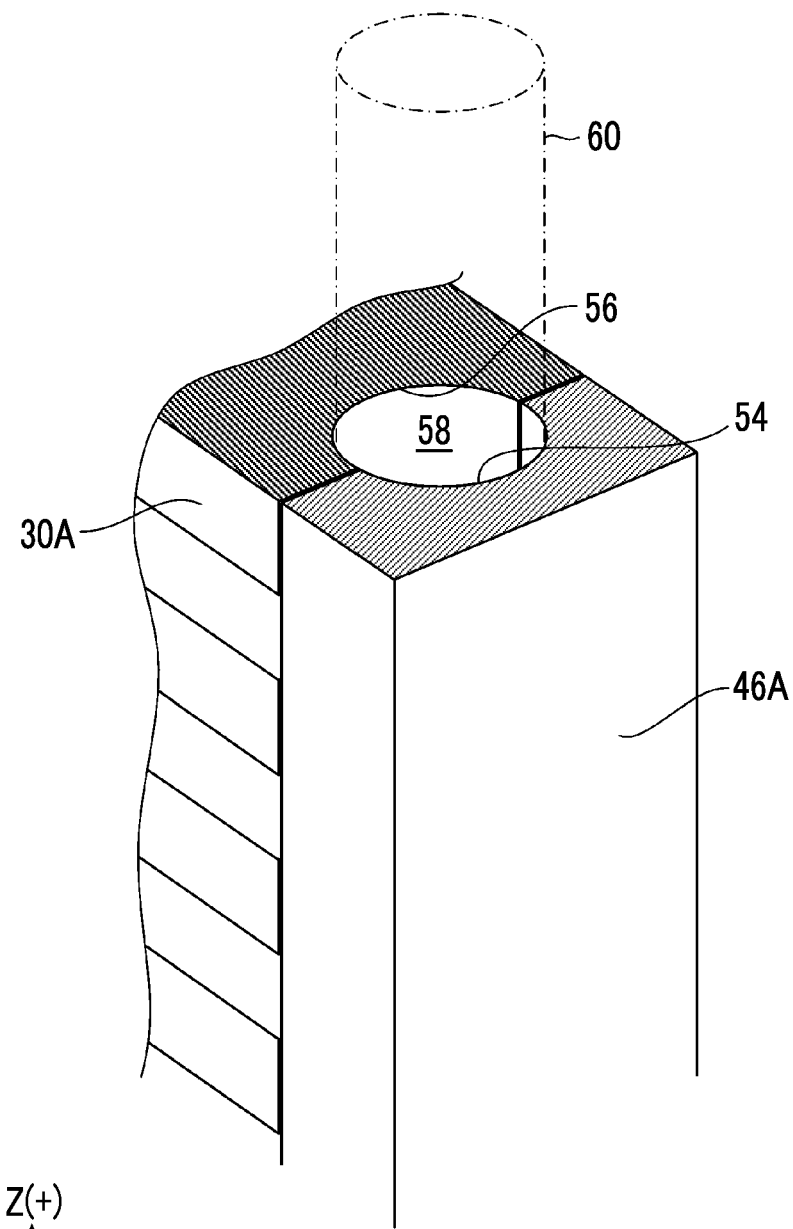
FIG. 11 is an enlarged cross sectional view of main parts, which illustrates an insertion passage into which a pin is inserted.

FIG. 8 illustrates a cylindrical pin 60 fitted from the through-hole 50 into the through-hole 52 via the insertion passage 58 (see FIG. 11). The pin 60 is fitted from the through-hole 50 into the through-hole 52 via the insertion passage 58 (see FIG. 11), an upper end part 60A of the pin 60 is fitted to an inner wall surface of the through-hole 50, a lower end part 60B of the pin 60 is fitted to an inner wall surface of the through-hole 52, and a portion of the pin 60 excluding the upper end part 60A and the lower end part 60B is fitted to the insertion passage 58. Accordingly, the plug 26 is prevented from coming off from the connector exterior case 28, and the linear portion 30A of the elliptical ring portion 30 is reinforced by the pin 60, causing a state where the deformation of the linear portion 30A is suppressed. In addition, the pin 60 is fastened to the elliptical ring portion 30 by a screw 62 (see FIG. 7) screwed from the lower end part 60B to the linear portion 30A of the elliptical ring portion 30. Accordingly, the pin 60 is prevented from falling off. Further, the upper end part 60A and the lower end part 60B of the pin 60 are composed of slopes so as not to protrude from the outer peripheral surface of the linear portion 46A. Herein, the pin 60 is an example of a shaft member, which is a component of the present invention, and is preferably made of a metal having high stiffness. In addition, the screw 62 is an example of a fastening member, which is a component of the present invention.

In addition, as illustrated in FIG. 8, the connector exterior case 28 comprises, in a rear end thereof, an opening portion 64 to which the universal cable 106 (see FIG. 3) is connected. In addition, an elastic O-ring 66 (see FIG. 10) is fitted to an outer peripheral surface of the universal cable 106, and the universal cable 106 is fitted into the opening portion 64 via the O-ring 66. The O-ring 66 is an example of a third sealing member that is disposed between an outer peripheral surface configuring an outer wall surface of the universal cable 106 and an inner peripheral surface configuring an inner wall surface of the opening portion 64 and is a component of the present invention. The O-ring 66 is also one of the plurality of sealing members that seal the inside of the exterior member 20, like the O-rings 36, 40, and 44.

When assembling the endoscope 100 illustrated in FIG. 1, the insertion part 102, the grip portion 104, the switch disposed member 108, and the universal cable 106 are inserted into the outside from the opening 27 (see FIG. 7) of the connector exterior case 28 via the opening portion 64 (see FIG. 8), starting from the insertion part 102. For this reason, the opening portion 64 of the connector exterior case 28 is configured in a size that allows the insertion part 102, the grip portion 104, the switch disposed member 108, and the universal cable 106 to be inserted therein. By configuring the opening portion 64 in such a size, it becomes easy to assemble the endoscope 100. In addition, even when disassembling the endoscope 100, it becomes easy to disassemble the endoscope. It is more preferable that the opening portion 64 has a size that allows the insertion even in a state where the operation switch 110 is disposed on the switch disposed member 108. That is, the inner diameter of the opening portion 64 may be set to be larger than the diameter of a circumscribed circle of the switch disposed member 108 including the operation switch 110 when viewed from a longitudinal axis direction of the universal cable 106.

Figure 12:
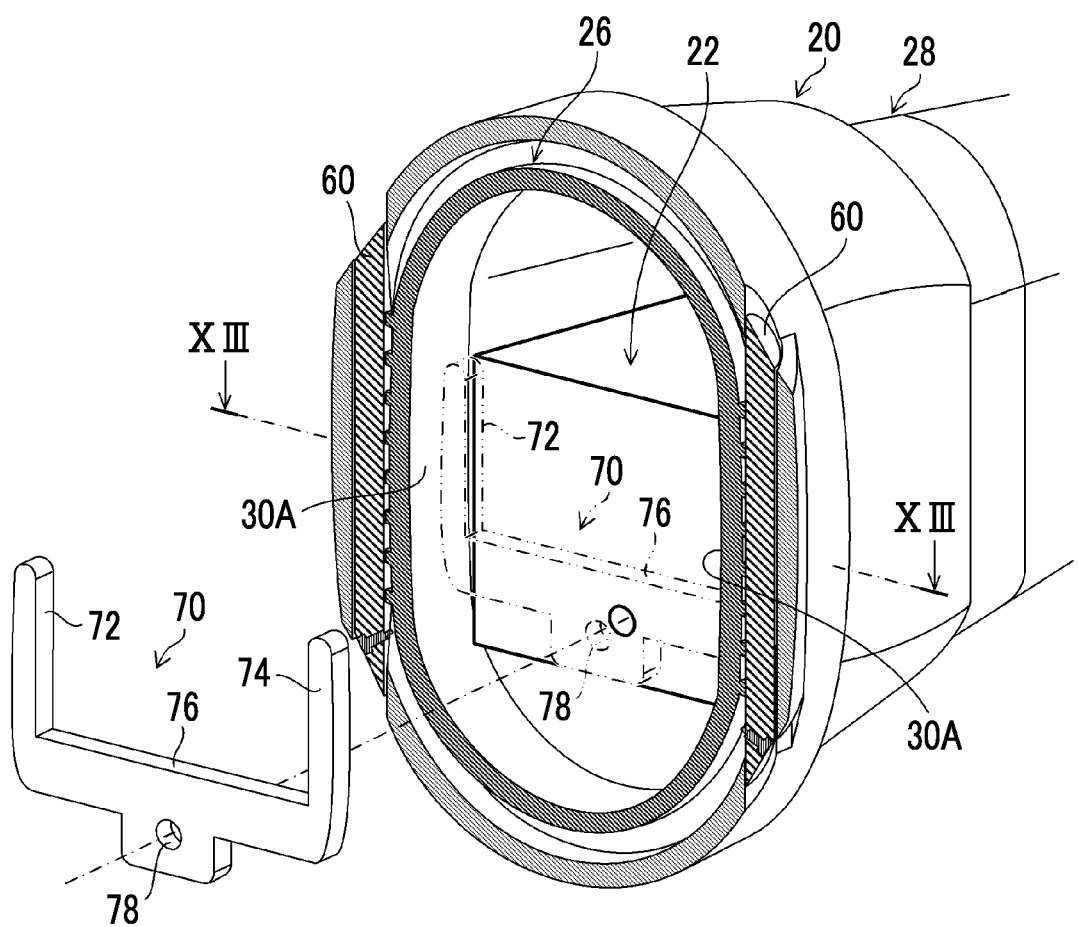
FIG. 12 is a perspective view of main parts, which illustrates a metal fitting disposed inside the plug.

FIG. 12 is a cross sectional perspective view of main parts, which illustrates a plate-shaped metal fitting 70 disposed inside the plug 26. In addition, FIG. 13 is a cross sectional view of main parts, taken along line XIII-XIII of FIG. 12.

As illustrated in FIGS. 12 and 13, the metal fitting 70 comprises a pair of reinforcing portions 72 and 74 extending in the up-and-down direction and a connecting portion 76 connecting the reinforcing portion 72 and the reinforcing portion 74 to each other. The reinforcing portion 72 and the reinforcing portion 74 are disposed at an interval in the right-and-left direction. The connecting portion 76 extends in the right-and-left direction, one end thereof is connected to a lower end of the reinforcing portion 72, and the other end thereof is connected to a lower end of the reinforcing portion 74. In addition, a center part of the connecting portion 76 comprises a hole 78, and the metal fitting 70 is fixed to the shield case 22 of FIG. 12 by a screw (not illustrated) inserted in the hole 78. The metal fitting 70 is an example of a reinforcing member, which is a component of the present invention. The metal fitting 70 may be fixed to a member other than the shield case 22, but it is preferable to fix the metal fitting to the shield case 22 since the metal fitting 70 can be stably disposed inside the exterior member 20.

The reinforcing portion 72 abuts against an inner peripheral surface of the linear portion 30A on the right, among the pair of linear portions 30A and 30A, and the reinforcing portion 74 abuts against an inner peripheral surface of the linear portion 30A on the left. In addition, as illustrated in FIG. 13, a position where the metal fitting 70 is disposed in a front-and-rear direction (X-direction) is set to the same position as a position where the O-ring 36 is disposed.

Next, the workings of the connector device 10 of the embodiment configured as described above will be described.

In a case where the connector device 10 is exposed in a vacuum state at a high temperature during sterilization or after sterilization, the internal pressure of the exterior member 20 becomes higher than the external pressure of the exterior member 20. At this time, a force caused by a differential pressure concentrates on the elliptical ring portion 30, which is a connecting part between the plug 26 and the connector exterior case 28. In addition, since the elliptical ring portion 30 is formed in a race track shape, the force concentrates on the linear portions 30A and 30A that have strength lower than the curved portions 30B and 30B. For this reason, the linear portions 30A and 30A try to deform outward, but the deformation of the linear portions 30A and 30A is suppressed by the pin 60. Accordingly, since the linear portions 30A and 30A can be prevented from being deformed or damaged by the internal pressure of the exterior member 20, infiltration of water into the exterior member 20 can be prevented.

As described above, with the connector device 10 of the embodiment, infiltration of water into the exterior member 20 can be prevented since the linear portion 46A of the elliptical ring portion 46 of the connector exterior case 28 comprises the through-holes 50 and 52, the inner peripheral surface of the linear portion 46A comprises the groove 54, which connects the through-hole 50 and the through-hole 52 to each other, the outer peripheral surface of the linear portion 30A of the elliptical ring portion 30 of the plug 26 comprises the groove 56, the groove 56 is disposed to face the groove 54 so that the insertion passage 58 is formed, the pin 60 is fitted into the through-hole 52 from the through-hole 50 via the insertion passage 58, and the pin 60 is fitted to the through-hole 50, the insertion passage 58, and the through-hole 52.

In addition, in a case where the plug 26 is pushed toward the front by the internal pressure of the exterior member 20 as shown with an arrow A of FIG. 13, the groove 56 tends to ride on the pin 60. For this reason, fitting portions 25 positioned at the linear portions 30A and 30A tend to deform inward, but the deformation of the fitting portions 25 is suppressed by the reinforcing portions 72 and 74 of the metal fitting 70. Accordingly, since the O-ring 36 is held in a state of being closely attached to the inner peripheral surface of the elliptical ring portion 46, the infiltration of water into the exterior member 20 can be more effectively prevented.

The pin 60 may have a prismatic shape, and the shape of the groove 56 may be a shape (polygon) corresponding to the shape of the pin 60. In this case, the occurrence of a problem that the groove 56 rides on the pin 60 can be suppressed. However, as in the embodiment, it is preferable that the pin 60 has a cylindrical shape and the groove 56 has a semicircular shape. In this case, a reaction force from the pin 60 can be dispersed on the wall surface of the groove 56.

In addition, in the connector device 10 of the embodiment, the shield case 22 is disposed to be spaced apart from the inner surface of the plug 26 and the inner surface of the connector exterior case 28 as being held by the exterior member 20 via the O-ring 44. With this configuration, the connector device 10 of the embodiment can obtain the following effects.

That is, in a case where the endoscope 100 comprising the connector device 10 is taken out from a high-pressure steam sterilizer, the temperature of the connector device 10 heated by the high-pressure steam sterilizer is gradually decreased by outside air. Herein, for example, in a case where a configuration in which the shield case 22 is in contact with the exterior member 20, in particular, the inner surface of the connector exterior case 28 is adopted, a temperature difference between the connector exterior case 28 and the shield case 22 is unlikely to occur in the process of decreasing the temperature after sterilization. Thus, moisture in the air inside the connector exterior case 28 adheres to an inner wall and a substrate of the shield case 22 and condensation occurs, causing a problem of adversely affecting the substrate. That is, condensation occurs also on an inner wall of the connector exterior case 28, but simultaneously with the condensation or without a time lag therebetween, condensation occurs on the inner wall and the substrate of the shield case 22.

On the contrary, in the connector device 10 of the embodiment, as the shield case 22 is held by the exterior member 20 only via the O-ring 44, the outer surface of the shield case 22 is disposed to be spaced apart from the inner surface of the plug 26 and the inner surface of the connector exterior case 28. In addition, in the connector device 10 of the embodiment, as the connector exterior case 28 accommodates the shield case 22 in a posture in which the long side 22A of the shield case 22 is aligned with the longitudinal axis 10a, a sufficient space is secured between an inner surface of the exterior member 20 and the outer surface of the shield case 22. Therefore, since condensation is unlikely to occur on the outer surface of the shield case 22 in the connector device 10 of the present embodiment, condensation on the substrate disposed inside the shield case 22 can be prevented.

In addition, in the connector device 10 of the embodiment, since the outer surface of the shield case 22 is disposed to be spaced apart from the inner surface of the plug 26 and the inner surface of the connector exterior case 28, internal stress caused by a temperature difference between the connector exterior case 28 and the shield case 22 can be reduced. Accordingly, heat cycle resistance attributable to steam sterilization improves.

In addition, in the connector device 10 of the embodiment, since a sufficient space is secured between the inner surface of the exterior member 20 and the outer surface of the shield case 22, time constant (relaxation time) representing time required for the heat of the high-pressure steam sterilizer to be transmitted to an electrical component such as a substrate increases. Accordingly, thermal stress on the electrical component can be reduced.

Although the plug 26 and the connector exterior case 28 respectively comprising the pair of linear portions 30A and 30A and the pair of linear portions 46A and 46A, which face each other due to the elliptical ring portions 30 and 46 formed in a race track shape, are given as examples of a preferable aspect in the embodiment, without being limited thereto, the present invention can be applied, for example, even to a plug and a connector exterior case comprising a pair of linear portions, which face each other due to a first connecting part and a second connecting part formed in a quadrangular shape in plan view.

In addition, although a configuration where the pair of linear portions 30A and 30A are parallel to each other and the pair of linear portions 46A and 46A are parallel to each other is described as a preferable aspect in the embodiment, the linear portions do not necessarily have to be parallel to each other insofar as the plug 26 and the connector exterior case 28 can be fitted and fixed via the pin 60.

In addition, although the shape of the first connecting part (corresponding to the elliptical ring portion 30) in plan view is a race track shape as a preferable aspect in the embodiment, the first connecting part is not limited to the shape. For example, in a case where the shape of the first connecting part in plan view is a perfect circle, the internal pressure of the exterior member is evenly applied to the entire periphery of the first connecting part. Thus, the deformation of the first connecting part can be suppressed.

In addition, the position where the metal fitting 70 is disposed in the front-and-rear direction is set to the same position as the position where the O-ring 36 is disposed as in FIG. 13 as a preferable aspect in the embodiment, without being limited thereto, but for example, may be set to the same position as a position where the pin 60 is disposed. However, in a case where the position where the metal fitting 70 is disposed in the front-and-rear direction is set to the same position as the position where the O-ring 36 is disposed, the deformation of the fitting portions 25 positioned at the linear portions 30A and 30A, among the recessed fitting portions 25 on the plug 26 side, to which the O-rings 36 are fitted, can be effectively prevented, which is preferable.

In addition, in the connector device 10 of the embodiment, the plug 26 and the connector exterior case 28, which configure the exterior member 20, are preferably made of, for example, a polyphenylsulfone resin, the light guide rod 12 and the pins 18 and 60 are preferably made of, for example, stainless steel, and the O-rings 36, 40, 44, and 66 are preferably made of, for example, highly heat-resistant fluororubber.

Although the present invention has been described hereinbefore, the present invention is not limited to the examples, and it is evident that various improvements and modifications may be made without departing from the gist of the present invention.

EXPLANATION OF REFERENCES

1: endoscope system
10: connector device
10a: longitudinal axis
12: light guide rod
13: bracket
14: image signal transmission unit
16: fiber cable
16A: light emission end
18: pin
20: exterior member
22: shield case
22A: long side
23: case wall part
24: power reception unit
25: fitting portion
26: plug
27: opening
28: connector exterior case
30: elliptical ring portion
30A: linear portion
30B: curved portion
32: mount portion
32A: linear portion
32B: curved portion
32C: linear portion
32D: side wall part
34: cylindrical portion
36: O-ring
38: lead-out hole
40: O-ring
42: lead-out hole
44: O-ring
46: elliptical ring portion
46A: linear portion
46B: curved portion
48: groove
50: through-hole
52: through-hole
54: groove
56: groove
58: insertion passage
60: pin
60A: upper end part
60B: lower end part
62: screw
64: opening portion
66: O-ring
70: metal fitting
72: reinforcing portion
74: reinforcing portion
76: connecting portion
78: hole
100: endoscope
102: insertion part
102A: distal end surface
104: grip portion
106: universal cable
108: switch disposed member
110: operation switch
114: observation part
116: observation window
118: light guide
118A: light emission end
118B: light incident end
120: image pick-up lens group
122: prism
124: solid-state imaging element
126: signal line
200: processor device for an endoscope
202: light source unit
204: image signal reception unit
206: image processing unit
208: monitor
210: processor side connector
212: connection hole
214: connection hole
216: power feed unit

What is claimed is:

1. A connector device for an endoscope comprising:
an exterior member that includes a plug which has an annular first connecting part forming a first opening in an end part thereof and a connector exterior case which has an annular second connecting part forming a second opening in an end part thereof,
wherein the first connecting part has at least a pair of first linear portions facing each other,
the second connecting part has at least a pair of second linear portions facing each other,
an outer peripheral surface of the first linear portion has a first groove along the first linear portion,
an inner peripheral surface of the second linear portion has a second groove along the second linear portion,
the second linear portion has a first through-hole that penetrates an outer peripheral surface and an inner peripheral surface of the second connecting part and is connected to one end side of the second groove and a second through-hole that penetrates the outer peripheral surface and the inner peripheral surface of the second connecting part and is connected to the other end side of the second groove,
the first groove and the second groove face each other so that an insertion passage along the first linear portion and the second linear portion is formed in a state where the outer peripheral surface of the first linear portion is fitted into the inner peripheral surface of the second linear portion so that the plug and the connector exterior case are connected to each other, and
the connector device for an endoscope further comprises a shaft member that is fitted into the second through-hole from the first through-hole via the insertion passage and is fitted to the first through-hole, the insertion passage, and the second through-hole.

2. The connector device for an endoscope according to claim 1,
wherein the pair of first linear portions are disposed to be parallel to each other, and
the pair of second linear portions are disposed to be parallel to each other.

3. The connector device for an endoscope according to claim 1, further comprising:
a fastening member that fastens the shaft member and the plug to each other.

4. The connector device for an endoscope according to claim 3, further comprising:
   a reinforcing member of which one end abuts against an inner peripheral surface of one first linear portion of the pair of first linear portions and the other end abuts against an inner peripheral surface of the other first linear portion.

5. The connector device for an endoscope according to claim 4,
   wherein a shield case is accommodated inside the exterior member, and the reinforcing member is fixed to the shield case.

6. The connector device for an endoscope according to claim 5, further comprising:
   a shaft-shaped member of which one end is fixed to the shield case;
   a first lead-out hole that is formed in the plug and leads the shaft-shaped member to an outside; and
   a second sealing member that is disposed between an outer wall surface of the shaft-shaped member and an inner wall surface of the first lead-out hole.

7. The connector device for an endoscope according to claim 6,
   wherein the shield case is disposed to be spaced apart from an inner surface of the exterior member as the shield case is held by the plug only via the second sealing member.

8. The connector device for an endoscope according to claim 6,
   wherein the second sealing member is an O-ring fitted to the outer wall surface of the shaft-shaped member.

9. The connector device for an endoscope according to claim 1, further comprising:
   a first sealing member disposed between an outer peripheral surface of the first connecting part and the inner peripheral surface of the second connecting part.

10. The connector device for an endoscope according to claim 9,
    wherein the first sealing member is an O-ring fitted to the outer peripheral surface of the first connecting part.

11. The connector device for an endoscope according to claim 1,
    wherein the shaft member is a cylindrical member.

12. The connector device for an endoscope according to claim 1,
    wherein the connector exterior case has an opening portion to which a universal cable extending from an endoscope is connected, and
    a third sealing member is disposed between an outer wall surface of the universal cable and an inner wall surface of the opening portion.

13. The connector device for an endoscope according to claim 12,
    wherein the third sealing member is an O-ring fitted to the outer wall surface of the universal cable.

14. The connector device for an endoscope according to claim 12,
    wherein the opening portion of the connector exterior case is formed in a size that allows the endoscope, the universal cable, and a switch disposed member provided at the universal cable to be inserted therein.

15. The connector device for an endoscope according to claim 1, further comprising:
    a light guide rod of which one end is fixed to the plug;
    a second lead-out hole that is formed in the plug and leads the light guide rod to an outside; and
    a fourth sealing member that is disposed between an outer wall surface of the light guide rod and an inner wall surface of the second lead-out hole.

16. The connector device for an endoscope according to claim 15,
    wherein the fourth sealing member is an O-ring fitted to the outer wall surface of the light guide rod.

* * * * *